United States Patent [19]

Warriner

[11] Plant 4,899

[45] Oct. 26, 1982

[54] ROSE PLANT—75-20364

[75] Inventor: William A. Warriner, Tustin, Calif.

[73] Assignee: Jackson & Perkins Co., Medford, Oreg.

[21] Appl. No.: 218,730

[22] Filed: Dec. 22, 1980

[51] Int. Cl.[3] ..... A01H 5/00

[52] U.S. Cl. ..... Plt./14

[58] Field of Search ..... Plt./14

*Primary Examiner*—Robert E. Bagwill

*Attorney, Agent, or Firm*—Klarquist, Sparkman, Campbell, Leigh, Whinston & Dellett

[57] ABSTRACT

A vigorous, well branched rose plant of upright habit with large, dark green mature foliage and grayed purple new foliage. Bud is long with blunt top. Petals are white with occasional green streaks on outer petals.

1 Drawing Figure

1

This present invention relates to a new and distinct variety of rose plant of the hybrid tea class which was originated by me by crossing the variety Evening Star, U.S. Plant Pat. No. 3,432, with the variety Coquete, U.S. Plant Pat. No. 4,019.

The primary objective of this breeding was to produce a new rose variety combining the growth habit of Coquette with flower opening and form of Evening Star, particularly suitable as a variety useful for production of cut blooms. This objective was substantially achieved along with other desirable improvements as evidenced by the following unique combination of characteristics which are outstanding in the new variety and which distinguish it from its parents as well as from all other varieties of which I am aware:

1. A vigorous, well branched, upright plant habit.
2. Large, dark green mature foliage, grayed purple new foliage. Differs from Coquette in that very little red pigment is evident on lower side of foliage.
3. A long, but blunt top bud, contrasted with pointed buds of Coquette and Evening Star.
4. Petal color more nearly white than Coquette and Evening Star.
5. Occasional green streaks on outer petals.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart except where ordinary dictionary significance of color is indicated.

Parentage:

*Seed parent.*—Evening Star, U.S. Plant Pat. No. 3,432.

*Pollen parent.*—Coquette, U.S. Plant Pat. No. 4,019.

Classification:

*Botanical.*—Rosa hybrid.

*Commercial.*—Hybrid tea.

2

FLOWER

Observations made from specimens grown at Irvine, Calif., in October of 1980. Plants grown in fiberglass greenhouse.

Blooming habit: Continuous.

Bud:

*Size.*—1¼" when petals start to unfurl.

*Form.*—Long, blunt top.

*Color.*—When sepals first divide, near white; outer petals sometimes show green areas near mid-ribs; when half blown, upper side of petals mostly white; lower side of petals mostly white.

*Sepals.*—Color: outer surface Near Green 138A; three appendaged sepals lightly appendaged; two unappendaged sepals hairy edged.

*Receptacle.*—Color: Green (138). Shape: funnel. Size: broad, small. Surface: smooth.

*Peduncle.*—Length: very long. Surface: prickly. Color: light green. Strength: stiff, erect.

*Opening.*—Petal edges curl back, causing outer petals to appear slightly pointed.

Bloom:

*Size.*—Large. Average open size 4½" to 5".

*Borne.*—Singly.

*Stems.*—Long, strong.

*Form.*—When first open, high centered. Permanence: retains its form to the end.

*Petalage.*—Number of petals under normal conditions: 30-35.

*Color.*—Center of flower: upper side of petals White. Reverse side of petals White. Base of petals, point of attachment Yellow (10A), lightening in color to (10D) away from point. This color tends to be reflected off petals showing in photograph of open and half open flowers. General tonality from a distance: White.

*Variegations.*—Some green streaks on outer petals.

*Discoloration.*—General tonality at end of first day, no change; third day, white.

*Fragrance.*—Very slight.

Petals:

*Texture.*—Thick.

*Shape.*—Nearly round.

*Form.*—Edges slightly quilled.

*Arrangement.*—Imbricated.

*Persistence.*—Drop off cleanly.

*Lastingness.*—On the plant, long. As cut flower, long.

Reproductive parts:

*Anthers.*—Medium. Color, yellow. Arrangement: regular around styles.

*Filaments.*—Color: white.

*Pollen.*—Lemon yellow.

*Styles.*—Color: white at base, purple near stigmas.

*Stigmas.*—Color: white.

PLANT

Form: Bush.

Growth: Very vigorous, upright.

Foliage: Number of leaflets on normal mid-stem leaves: 5–7.

*Size.*—Very large.

*Quantity.*—Abundant.

*Color.*—New foliage: Near Greyed Purple 187B. Old foliage: Green 136B. Not as reddish on underside of maturing leaves as that of Coquette.

Leaflets:

*Shape.*—Oval pointed.

*Texture.*—Upper side, leathery.

*Edge.*—Serrated.

*Serration.*—Single, small.

*Petiole.*—Rachis: color, green. Underside: prickles.

*Stipules.*—Long, bearded.

*Disease resistance.*—Normally resistant to mildew under normal growing conditions at Irvine, Calif.

Wood:

*New wood.*—Color: light green. Bark: smooth.

*Old wood.*—Color: green. Bark: smooth.

Prickles:

*Quantity.*—On main stalks from base, ordinary. On laterals from stalk, ordinary.

*Form.*—Long base, hooked downward.

*Color when young.*—Brown.

*Position.*—Irregular.

Small prickles:

*Quantity.*—On main stalks, none. On laterals, none.

I claim:

1. A new and distinct variety of rose plant of the hybrid tea class, substantially as herein shown and described, characterized particularly as to novelty by the unique combination of its vigorous, upright plant producing blunt top buds of very white petals, occasionally having green streaks on outer petals.

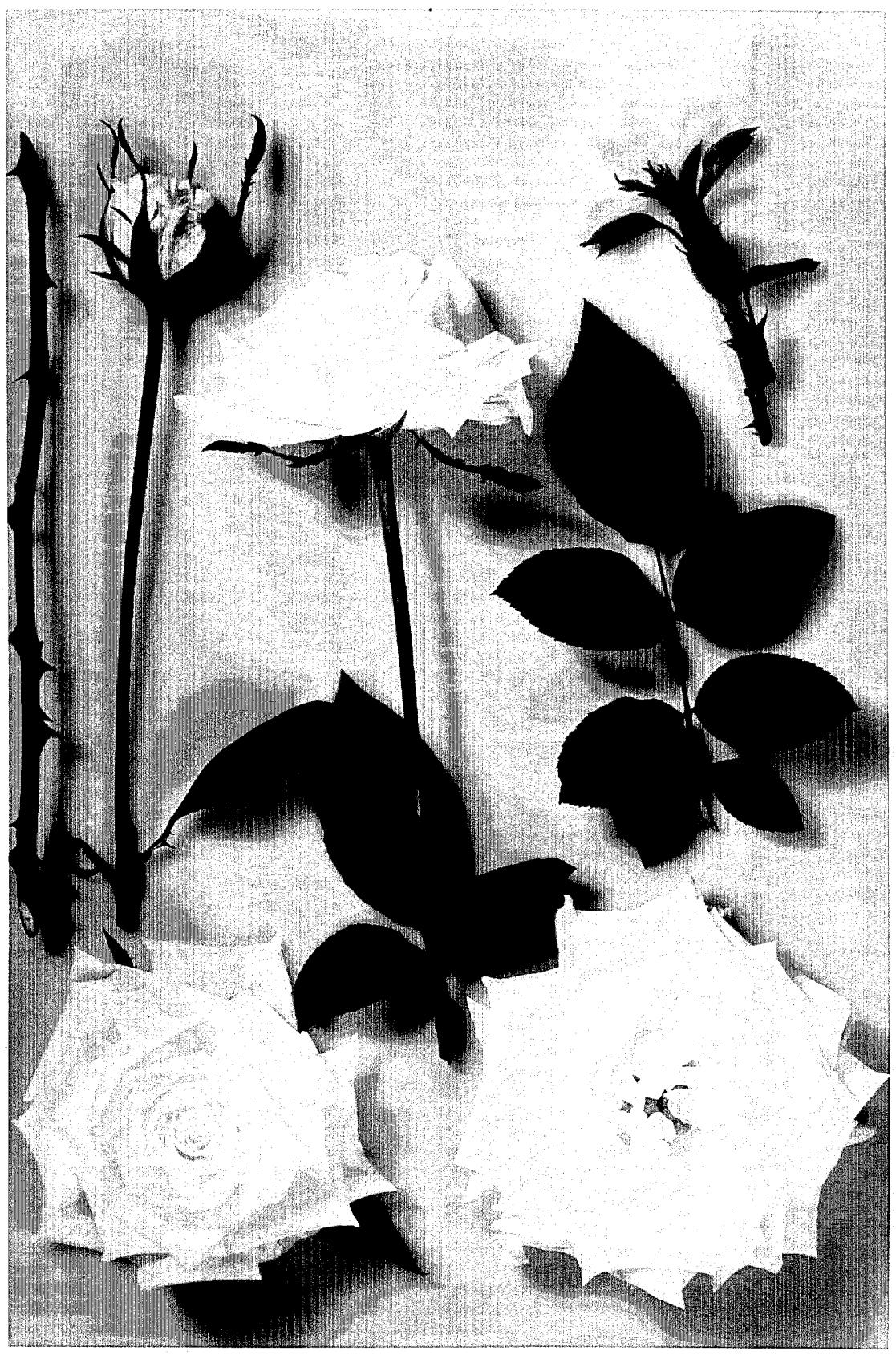

* * * * *